United States Patent [19]

Gutierrez et al.

[11] Patent Number: 5,693,854
[45] Date of Patent: Dec. 2, 1997

[54] ETHYLENE DICYSTEATE SEQUESTRANTS AND METHODS FOR PREPARATION

[75] Inventors: Eddie Nelson Gutierrez, Midland Park; Shang-Ren Wu, Mahwah; Robert Vermeer, Nutley, all of N.J.

[73] Assignee: Lever Brothers Company, Division of Conopco, Inc.

[21] Appl. No.: 579,283

[22] Filed: Dec. 27, 1995

[51] Int. Cl.$^6$ .................................................. C07C 309/04
[52] U.S. Cl. ............................................................ 562/102
[58] Field of Search .............................................. 562/102

[56] References Cited

U.S. PATENT DOCUMENTS

| | | | |
|---|---|---|---|
| 3,151,084 | 9/1964 | Schlitz et al. | 510/480 |
| 3,920,564 | 11/1975 | Grecsek | 510/332 |
| 4,397,776 | 8/1983 | Ward | 510/407 |
| 4,560,492 | 12/1985 | Curry et al. | 510/340 |
| 4,704,233 | 11/1987 | Hartman et al. | 510/337 |
| 5,183,590 | 2/1993 | Carter et al. | 252/392 |
| 5,472,642 | 12/1995 | Gutierrez | 252/545 |

FOREIGN PATENT DOCUMENTS 708 079   4/1996   European Pat. Off. .

*Primary Examiner*—Joseph Conrad
*Attorney, Agent, or Firm*—James J. Farrell

[57] ABSTRACT

Novel compounds useful as sequestrants as well as builders for detergent compositions and methods for their preparation are disclosed.

15 Claims, No Drawings

ETHYLENE DICYSTEATE SEQUESTRANTS AND METHODS FOR PREPARATION

FIELD OF THE INVENTION

The present invention relates to improved detergent compositions. Specifically, it relates to improved laundry detergent compositions. More specifically, it relates to improved laundry detergent compositions containing ethylene dicysteic acid, a novel non-phosphorous chelant, which assists in the removal of food, beverage and certain other organic stains from fabrics during the laundry process. Ethylene dicysteate (EDC) can be used as a replacement for all or part of the chelants currently used in many existing laundry products, thereby yielding detergent formulations having reduced phosphorus content. The difficulties with phosphorus-containing compositions are well-documented.

Accordingly, it is highly desirable to be able to formulate detergent compositions with reduced levels of phosphorous-containing components which are potentially biodegradable, but still exhibit excellent cleaning and stain removal performance.

In addition, while the use of chelants in detergent compositions is generally desirable for enhanced stain removal, there is usually an efficacy/biodegradability trade-off with chelants and sequestrants. For example, chelants that provide the best stain removal tend to be totally non-biodegradable, while those that exhibit some level of biodegradability are poor in terms of stain removal.

It is an object of the present invention to provide novel laundry detergent compositions containing a non-phosphorous biodegradable chelant. It is another object of the present invention to provide improved laundry detergent compositions which exhibit excellent stain removal characteristics. It is a final object of the present invention to provide a novel effective chelant/sequestrant useful in detergent, personal product, cosmetic, food, oral hygiene, pharmaceutical and industrial compositions.

These and other objects of the invention will become readily apparent from the detailed description that follows.

BACKGROUND OF THE INVENTION

The use of aminopolycarboxylates as builders and laundry detergent additives is generally disclosed in the art. For example, U.S. Pat. No. 4,560,491 discloses laundry detergent compositions, essentially free of phosphate detergency builders, containing an aluminosilicate or organic detergency builder and from about 0.5% to about 10% by weight of the chelant, HEDTA.

U.S. Pat. No. 4,397,776 discloses liquid laundry detergent compositions having chelating agents which include aminopolycarboxylates such as NTA, EDTA, DTPA and HEDTA.

U.S. Pat. No. 3,920,564 discloses softener/detergent formulations containing surfactants, quaternary ammonium or diamine fabric softeners, and a builder salt selected from aminopolycarboxylates and/or sodium citrate. Examples of suitable aminopolycarboxylates include NTA, EDTA and HEDTA.

U.S. Pat. No. 3,151,084 discloses detergent compositions in which solubility is said to be improved by the addition of 0.25% to 4% of a mixture of EDTA and a solubilizing agent selected from salts of N,N-di(2-hydroxyethyl) glycine, iminodiacetic acid, NTA and HEDTA.

U.S. Pat. No. 4,703,233 discloses ethylenediamine N,N'-disuccinic acid and salts as a detergent additive which is said to enhance the removal of food and beverage stains.

U.S. Pat. No. 5,183,590 discloses N-(hydroxysuccinyl) cysteic acid as a corrosion inhibitor for aqueous systems.

None of these references disclose or recognize the compositions of the present invention or the unique ability of EDC to assist in the removal of stain from fabric.

In addition, none of these references disclose or recognize EDC as a novel potentially readily biodegradable chelant/sequestrant suitable for detergent, personal product, cosmetic, food, oral hygiene, pharmaceutical and industrial applications.

SUMMARY OF THE INVENTION

One embodiment of the invention specifically relates to laundry detergent compositions comprising:

(a) from about 1% to about 75% by weight of a detergent surfactant selected from the group consisting of anionic surfactants, nonionic surfactants, zwitterionic surfactants, ampholytic surfactants, cationic surfactants, and mixtures thereof;

(b) from about 0% to about 80% by weight of a detergency builder; and (c) from about 0.1% to about 50% by weight of ethylene dicysteic acid or the alkali metal, alkaline earth, ammonium or substituted ammonium salts thereof, as well as mixtures thereof; and (d) the remainder is water and additional optional detersive ingredients.

The second embodiment of the invention relates to a novel non-phosphorous potentially readily biodegradable chelant suitable for detergent, personal product, oral hygiene, cosmetic, food, pharmaceutical and industrial applications. The novel chelant is known as ethylene dicysteic acid, abbreviated as EDC.

DETAILED DESCRIPTION OF THE INVENTION

A. The Detergent Surfactant System

The amount of detergent surfactant included in the detergent compositions of the present invention can vary from about 1% to about 75% by weight of the composition depending upon the particular surfactant(s) used, the type of composition to be formulated (e.g. granular, liquid or concentrate) and the effects desired. Preferably, the detergent surfactant(s) comprises from about 5% to about 60% by weight of the composition. The detergent surfactant can be nonionic, anionic, ampholytic, zwitterionic or cationic. Mixtures of these surfactants can also be used.

B. Detergent Builders

Detergent compositions of the present invention contain inorganic and/or organic detergent builders to assist in mineral hardness control. These builders comprise from about 0% to about 80% by weight of the compositions. Built liquid formulations preferably comprise from about 0% to about 30% by weight of detergent builder, while built granular formulations preferably comprise from about 10% to about 50% by weight of detergent builder.

Suitable detergent builders include crystalline aluminosilicate ion exchange materials having the formula:

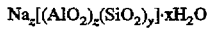

$$Na_z[(AlO_2)_z(SiO_2)_y]\cdot xH_2O$$

wherein z and y are at least about 6, the mole ratio of z to y is from about 1.0 to about 0.5; and x is from about 10 to about 264. Amorphous hydrated aluminosilicate materials useful herein have the empirical formula:

$$M_z(zAlO_2 \cdot ySiO_2)$$

wherein M is sodium, potassium, ammonium or substituted ammonium, z is from about 0.5 to about 2, and y is 1; this material has a magnesium ion exchange capacity of at least about 50 milligram equivalents of $CaCO_3$ hardness per gram of anhydrous aluminosilicate.

Aluminosillicate ion exchange materials useful herein are commercially available. These aluminosilicates can be crystalline or amorphous in structure and can be naturally-occurring or synthetically derived. A method for producing aluminosillicate ion exchange materials is disclosed in U.S. Pat. No. 3,985,669, Krummel et al, issued Oct.12, 1976, incorporated herein by reference. Preferred synthetic crystalline aluminosilicate ion exchange materials useful herein are available under the designations Zeolite A, Zeolite P (B), and Zeolite X. In an especially preferred embodiment, the crystalline aluminosilicate ion exchange material has the formula:

$$Na_{12}[(AlO_2)_{12}(SiO_2)_{12}] \cdot xH_2O$$

wherein x is from about 20 to about 30, especially about 27.

Other detergency builders useful in the present invention include the alkali metal silicates, alkali metal carbonates, phosphates, polyphosphates, phosphonates, polyphosphonic acids, $C_8$–$C_{18}$ alkyl monocarboxylic acids, polycarboxylic acids, alkali metal ammonium or substituted ammonium salts thereof and mixtures thereof. Preferred are the alkali metal salts of the above, especially sodium.

Useful water-soluble, nonphosphorous organic builders include the various alkali metal, ammonium and substituted ammonium polyacetates, carboxylates, polycarboxylates and polyhydroxysulfonates. Examples of polyacetate and polycarboxylate builders are the sodium, potassium, lithium, ammonium and substituted ammonium salts of ethylenediamine tetraacetic acid, ethylenediamine disuccinic acid (EDDS), nitrilotriacetic acid (NTA), oxydisuccinic acid (ODS), mellitic acid, carboxymethyloxysuccinic acid, (CMOS), benzene polycarboxylic acids and citric acid. For purposes of defining the invention, the organic detergent builder component which may be used herein does not include EDC or its salts, although EDC can be used as a builder as well as a chelant/sequestrant if desired.

C. Ethylene Dicysteic Acid (EDC) or Salts Thereof (The Invention)

The compositions of the invention contain, as an essential component, from about 0.1% to about 50%, preferably from about 0.2% to about 15%, more preferably from about 0.3% to about 10%, of ethylene dicysteic acid (EDC) or the alkali metal, alkaline earth metal, ammonium or substituted ammonium salts thereof, or mixtures thereof. Preferred EDC compounds for granular detergent compositions are the free acid and the corresponding sodium salt forms as well as mixtures thereof. Examples of such preferred sodium salts of EDC include NaEDC, $Na_2EDC$, $Na_3EDC$ and $Na_4EDC$, wherein Na is sodium. Preferred EDC compounds for liquid detergent compositions are the free acid and the corresponding substituted ammonium or potassium salt forms thereof. Examples of such preferred salts of EDC include (MEA) EDC, $(MEA)_2$ EDC, $(MEA)_3$ EDC, $(MEA)_4$ EDC, (TEA) EDC, $(TEA)_2$ EDC, $(TEA)_3$, EDC, $(TEA)_4$ EDC, $(DEA)_4$ EDC, $(K)_4$ EDC and the like, wherein MEA is monoethanolamine, DEA is diethanolamine, TEA is triethanolamine and K is potassium.

The structure of the acid form of EDC is as follows:

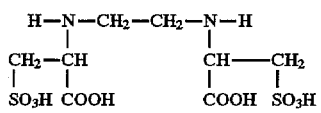

The structure of the sodium salt form of EDC is as follows:

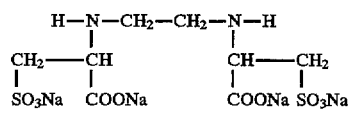

The structure of the MEA form of EDC is as follows:

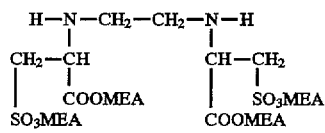

wherein MEA is monoethanolamine represented as $_+NH_3CH_2CH_2OH$.

The chelant/sequestrant of the invention, EDC, can be prepared from readily available fairly inexpensive raw materials such as cysteic acid (3-sulfoalanine or α-amino-β-sulfopropionic acid) and 1,2-dibromoethane (ethylenedibromide) as follows:

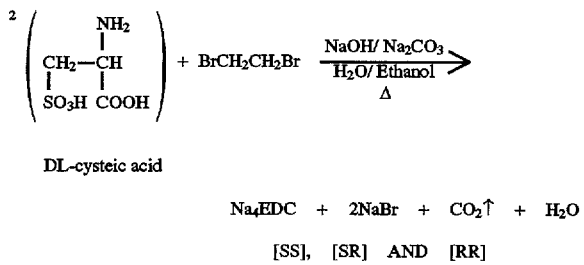

DL-cysteic acid $$Na_4EDC + 2NaBr + CO_2\uparrow + H_2O$$

[SS], [SR] AND [RR]

Cysteic acid can be prepared from cysteine or cystine by oxidation with bromine in water. Cysteine is prepared from the hydrolysis of proteins and cystine is formed by air oxidation in alkaline water solutions of cysteine.

The synthesis of EDC from DL-cysteic acid yields a mixture of three optical isomers, namely; (SS), (SR) and (RR). This is due to the presence of two asymmetric carbon atoms. Also, it is known that the biodegradation of certain amino polycarboxylates appears to be optical isomer-specific,with the (SS) isomer degrading most rapidly and extensively followed by the (SR) isomer and the (RR) isomer. Without being bound by theory, it is generally believed that the (SS) isomer of EDC degrades most quickly and readily.

The (S,S) isomer of EDC can be prepared from L-cysteic acid monohydrate and 1,2dibromoethane as follows:

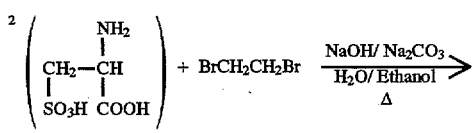

L-cysteic acid

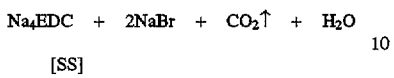

[SS]

Alternatively, EDC may be prepared from cystine and 1,2-dibromoethane to afford a polymeric material which can be oxidized to EDC as follows:

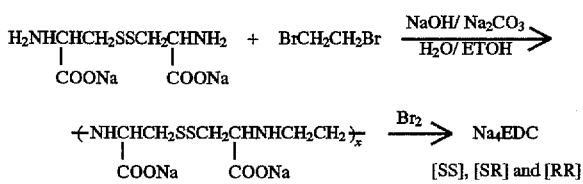

where x is > 0

The chelant/sequestrant, EDC, possess excellent stain removal characteristics, especially on polyphenolic stains such as tea, coffee, blueberry, monello juice, strawberry and the like. EDC was found to provide stain removal performance equivalent to, or superior to . . . 1, 2 and 3 nitrogen containing polycarboxylates such as NTA, EDTA and DETPA which are currently used in many existing laundry products. By using EDC as a replacement for such chelants, it is now possible to formulate detergent compositions which contain reduced levels of phosphorous-containing components while still exhibiting excellent cleaning and stain removal characteristics.

Without being bound by theory, it is believed that ethylene dicysteic acid and its salts, which are contained in the compositions of the present invention, act to chelate metal ions such as iron, manganese, zinc, copper, etc. which are constituents of certain organic stains. This, in turn, makes the stains easier to remove from the fabrics. It is also believed that such metal ions, which are always present in various amounts in wash liquids from pipes, environment, detergent ingredients, washing machines, dyes, soils, etc., have a detrimental effect on soils and stains, particularly on polyphenolic stains, such as wine, tea, grape juice, blueberry juice, coffee and the like, making such stains darker and more difficult to remove. The presence of EDC however acts to chelate such metal ions in the wash liquor enabling detergent materials to function more effectively and preventing stain metal interactions resulting in improved performance and cleaning. It is further believed that EDC can act to stabilize stains in the wash solution. Whatever the mechanism may be, EDC has been shown to facilitate the removal of stain from fabric. This finding has not been disclosed in the art.

It should be noted that other EDC derivatives can be easily prepared by the methods of the present invention. For example, 1,2-dibromoethane can be replaced with epichlorohydrin, 1,3-dichloro-2-propanol or 1,3-dibromo-2-propanol. Subsequent reaction with DL-cysteic acid or L-cysteic and monohydrate in the presence of base, water and ethanol can give a novel EDC derivative known as 2-hydroxypropylene dicysteic acid tetrasodium salt (HPDC).

The structue of the acid form of HPDC is as follows:

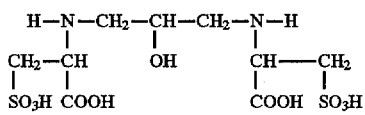

The structure of the sodium salt form of HPDC is as follows:

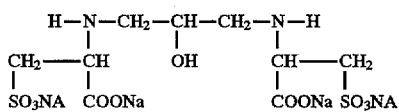

The general reaction scheme for HPDC is as follows:

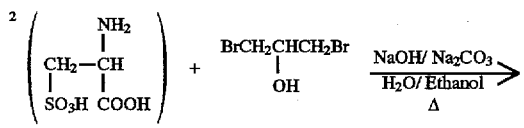

DL-cysteic acid

[SS], [SR] AND [RR]

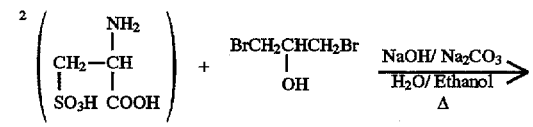

L-cysteic acid

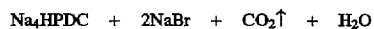

[SS]

The synthesis of HPDC from DL-cysteic acid yields a mixture of three optical isomers, namely; (SS), (SR) and (RR). This is due to the presence of two asymmetric carbon atoms. Also, it is known that the biodegradation of certain amino polycarboxylates appears to be optical isomer-specific, with the (SS) isomer degrading most rapidly and extensively followed by the (SR) isomer and the (RR) isomer. Without being bound by theory, it is generally believed that the (SS) isomer of HPDC degrades most quickly and readily.

Since HPDC is an EDC derivative, it can be easily substituted for EDC in the formulations of the present invention. Also, the home and industrial applications of HPDC can be substituted for EDC as well. In fact, by simple experimentation to those skilled in the art, additional unique synergies and benefits of HPDC can be easily determined.

D. Optional Detersive Ingredients

Other additional optional ingredients which can be present in detergent compositions of the invention (in their conventional art-established levels for use generally from 0% to about 50% by weight of the detergent composition), include solvents, hydrotropes, solubilizing agents, processing aids, soil-suspending agents, corrosion inhibitors, dyes, fillers, optical brighteners, germicides, pH-adjusting agents, enzymes, enzyme-stabilizing agents, perfumes, fabric softening components, static control agents, dispersing agents, suds suppressing agents, thickening agents, abrasive agents, viscosity control agents, solubilizing/clarifying agents, sunscreens/UV absorbers, phase regulants, foam boosting/stabilizing agents, antioxidants, metal ions, buffering agents, color speckles, encapsulation agents, deflocculating polymers, skin protective agents, dye transfer agents, color care agents, co-sequestrants, co-chelants, bleaching agents, bleach activators, bleach stabilizers and the like.

Materials that provide clay soil removal/anti-redeposition benefits can also be incorporated in the detergent compositions of the invention and are particularly useful in liquid compositions of the invention. These clay soil removal/anti-redeposition agents are usually included at from about 0.1% to about 10% by weight of the composition.

One group of preferred clay soil removal/anti-redeposition agents are the ethoxylated amines disclosed in U.S. Pat. No. 4,597,898. Soil release agents, such as those disclosed in the art to reduce oily staining of polyester fabrics, may also be used in the compositions of the present invention. U.S. Pat. No. 3,962,152 discloses copolymers of ethylene terephthalate and polyethylene oxide terephthalate as soil release agents. Cellulose ethers and various other soil release agents are also useful.

Many additional essential and optional ingredients that are useful in the present invention are those described in McCutcheon's, *Detergents and Emulsifiers* (Vol. 1) and McCutcheon's, *Functional Materials* (Vol. 2), 1995 Annual Edition, published by McCutcheon's MC Publishing Co., as well as the CTFA (Cosmetic, Toiletry and Fragrance Association) 1992 International Buyers Guide, published by CFTA Publications and OPD 1993 Chemicals Buyers Directory 80th Annual Edition, published by Schnell Publishing Co. which are all incorporated herein by reference.

Detergent Formulations

Granular detergent compositions embodying the present invention can be formed by conventional techniques, i.e. by slurrying the individual components in water and then atomizing and spray-drying the resultant mixture, or by pan or drum agglomeration of the ingredients. Granular formulations preferably comprise from about 5% to about 60% of detergent surfactant selected from the group consisting of anionic surfactants, nonionic surfactants, and mixtures thereof.

Liquid compositions of the present invention can contain water and other solvents. Low molecular weight primary or secondary monohydric alcohols are exemplified as methanol, ethanol, propanol, and isopropanol. Monohydric alcohols are preferred for solubilizing the surfactant, but polyols, containing from about 2 to about 6 carbon atoms and from about 2 to about 6 hydroxy groups, can be used to provide improved enzyme stability (if enzymes are included in the composition). Examples of such polyols include propylene glycol, ethylene glycol, glycerine and sorbitol. Ethanol and propylene glycol are particularly preferred alcohols.

The liquid compositions preferably comprise from about 5% to about 60% of detergent surfactant, about 1% to about 30% of builder and about 0.2% to about 15% ethylene dicysteic acid or salts thereof.

Useful detergency builders in liquid compositions include the alkali metal silicates, alkali metal carbonates, polyphosphonic acids, $C_8$–$C_{18}$ alkyl monocarboxylic acids, polycarboxylic acids, alkali metal, ammonium or substituted ammonium salts thereof, and mixtures thereof. Preferred liquid compositions contain from about 1% to about 30% of detergency builders selected from the group consisting of $C_8$–$C_{18}$ alkyl monocarboxylic acids, polycarboxylic acids and mixtures thereof.

Particularly, preferred liquid compositions contain from about 5% to about 18% of a $C_8$–$C_{18}$ monocarboxylic (fatty) acid and from about 0.2% to about 10% of a polycarboxylic acid, preferably citric acid, and provide a solution pH of from about 6 to about 10, preferably from about 6.5 to about 8.5 at a 1% concentration in water.

Preferred liquid compositions are substantially free of inorganic phosphates or phosphonates. As used in this context "substantially free" means that the liquid compositions contain less than about 0.5% by weight of an inorganic phosphate- or phosphonate-containing compound.

Many additional essential and optional ingredients that are useful in the liquid detergent compositions of the present invention are those described in McCutcheon's, *Detergents and Emulsifiers* (Vol. 1) and McCutcheon's, *Functional Materials* (Vol. 2), 1995 Annual Edition, published by McCutcheon's MC Publishing Co., as well as the CTFA (Cosmetic, Toiletry and Fragrance Association) 1992 International Buyers Guide, published by CFTA Publications and OPD 1993 Chemicals Buyers Directory 80th Annual Edition, published by Schnell Publishing Co. which are all incorporated herein by reference.

In a laundry method aspect of the invention, typical laundry wash water solutions comprise from about 0.1% to about 2% by weight of the detergent compositions of the invention. Fabrics to be laundered are agitated in these solutions to improve cleaning and stain removal characteristics of detergent compositions.

A liquid detergent composition might contain (all percentages by weight):

(1) 1–75% detergent surfactant system;

(2) 0–80% builder;

(3) 0–40% electrolyte;

(4) 0–5% enzyme;

(5) 0–15% enzyme stabilizer;

(6) 0–20% phase regulant;

(7) 0.1–50% EDC;

(8) water and additional optional ingredients to 100%.

A preferred liquid detergent composition might contain (all percentages by weight):

(1) 5–60% detergent surfactant system;

(2) 1–30% builder;

(3) 0–30% electrolyte;

(4) 0.01–4% enzyme;

(5) 00.1–14% enzyme stabilizer;

(6) 0–18% phase regulant;

(7) 0.2–15% EDC;

(8) water and additional optional ingredients to 100%

Powdered detergent composition might contain the following (all percentages by weight):

(1) 1–75% detergent surfactant system (2) 0–80% builder;

(3) 0–30% buffer salt;

(4) 0–30% sulfate;

(5) 0–20% bleach system;

(6) 0–4% enzyme;

(7) 0.1–50% EDC;

(8) water and additional optional ingredients to 100%.

A preferred powdered detergent composition might contain the following (all percentages by weight):

(1) 5–60% detergent surfactant system (2) 0–50% builder;

(3) 0–28% buffer salt;

(4) 0–28% sulfate;

(5) 0–18% bleach system;

(6) 0–3.5% enzyme;

(7) 0.1–15% EDC;

(8) water and additional optional ingredients to 100%.

The EDC component of the above formulations can be replaced by EDC trimer, HPDC or mixtures thereof at the same levels of incorporation if desired.

Home Application and Use

The EDC chelant/sequestrant and its salts of the present invention are useful in a variety of detergent, personal product, cosmetic, oral hygiene, food, pharmacological and industrial compositions which are available in many types and forms. Preferred compositions, however, are detergent compositions.

A classification according to detergent type would consist of heavy-duty detergent powders, heavy-duty detergent liquids, light-duty liquids (dishwashing liquids), institutional detergents, specialty detergent powders, specialty detergent liquids, laundry aids, pretreatments aids, after treatment aids, presoaking products, hard surface cleaners, carpet cleansers, carwash products and the like.

A classification according to personal product type would consist of hair care products, bath products, cleansing products, skin care products, shaving products and deodorant/antiperspirant products.

Examples of hair care products include, but are not limited to rinses, conditioners, shampoos, conditioning shampoos, antidandruff shampoos, antilice shampoos, coloring shampoos, curl maintenance shampoos, baby shampoos, herbal shampoos, hair loss prevention shampoos, hair growth/promoting/stimulating shampoos, hairwave neutralizing shampoos, hair setting products, hair sprays, hair styling products, permanent wave products, hair straightening/relaxing products, mousses, hair lotions, hair tonics, hair pomade products, brilliantines and the like.

Examples of bath products include, but are not limited to bath oils, foam or bubble bathes, therapeutic bathes, after bath products, after bath splash products and the like.

Examples of cleansing products include, but are not limited to shower cleansers, shower gels, body shampoos, hand/body/facial cleansers, abrasive scrub cleansing products, astringent cleansers, makeup cleansers, liquid soaps, toilet soap bars, synthetic detergent bars and the like.

Examples of skin care products include, but are not limited to hand/body/facial lotions, sunscreen products, tanning products, self-tanning products, aftersun products, masking products, lipsticks, lip gloss products, rejuvenating products, antiaging products, antiwrinkle products, anticellulite products, antiacne products and the like.

Examples of shaving products include, but are not limited to shaving creams, aftershave products, preshave products and the like.

Examples of deodorant/antiperspirant products include, but are not limited to deodorant products, antiperspirant products and the like.

A classification according to oral hygiene type would consist of, but is not limited to mouthwashes, pre-brushing dental rinses, post-bushing rinses, dental sprays, dental creams, toothpastes, toothpaste gels, toothpowders, dental cleansers, dental flosses, chewing gums, lozenges and the like.

The EDC chelant/sequestrant of the present invention are also useful in softening compositions such as liquid fabric softeners, fabric softening rinses, fabric softening sheets, tissue papers, paper towels, facial tissues, sanitary tissues, toilet paper and the like.

A classification according to composition form would consist of aerosols, liquids, gels, creams, lotions, sprays, pastes, roll-on, stick, tablet, powdered and bar form.

Industrial Application and Use

The EDC chelant/sequestrant and its salts of the present invention are useful in a variety of compositions as above. More specifically, EDC is useful as chelants of heavy metal and hardness ions, scale inhibiting agents, corrosion inhibiting agents, deflocculating/dispensing agents, stain removal agents, bleach stabilizing agents, protecting agents of peroxygen liable ingredients, thickener/viscosity modifying agents, crystal growth modification agents, sludge modification agents, surface modification agents, processing aids, electrolyte, hydrolytic stability agents, alkalinity agents and the like. The EDC chelant/sequestrant and its salts of the present invention are also useful for certain industrial applications such as acid cleaners, aluminum etching, boiler cleaning, water treatment, bottle washing, cement modification, dairy cleaners, desalination, electrochemical machining, electroplating, metal finishing, paper mill evaporations, oil field water treatment, paper pulp bleaching, pigment dispersion, trace metal carrier for fertilizers, irrigation, circuit cleaning and the like.

The following examples further describe and demonstrate the preferred embodiments that are within the scope of the present invention. The examples are given solely for the purpose of illustration and are not to be construed as being limiting to the present invention since many variations are possible without departing from the spirit and scope of the invention.

The following non-limiting examples illustrate the present invention.

EXAMPLE 1

Preparation of Ethylene Dicysteate (EDC) and Ethylene Dicysteate Trimer 24 g (0.128 mol) of cysteic acid was dissolved in 160 ml of water and 10.2 g (0.255 mol) of sodium hydroxide was added. After dissolution, 6.8 g (0.064) sodium carbonate was added, followed by 80 ml ethanol. While refluxing the solution, 14.4 g (0.077 mol) dibromoethane was added gradually during a period of 4 hours, followed by refluxing overnight. An additional 14.4 g (0.077 mol) of dibromoethane was added, followed by all-day reflux. The solution was distilled to remove solvents and the resulting solid was found to contain a mixture of ethylene dicysteate and ethylene dicysteate trimer as well as salt, and some unreacted cysteic acid.

Electrospray Mass Spectrometry (EMS) Analysis I

M=452, $Na_4$ EDC (crude mixture before purification)

|  | M/Z |
|---|---|
| $(M-2Na + 1H)^-$ | 407 |
| $(M-3Na + 2H)^-$ | 385 |
| $(M-4Na + 3H)^-$ | 363 |
| $(M-2Na + 1H)^{-2}$ | 203 |
| $(M-3Na + 2H)^{-2}$ | 192 |
| $(M-4Na + 3H)^{-2}$ | 181 |

T=691, $Na_6$ EDC Trimer (crude mixture before purification)

$$NaO_3SCH_2\underset{\underset{COONa}{|}}{C}HNHCH_2CH_2\underset{\underset{\underset{CH_2SO_3Na}{|}}{CHCOONa}}{N}CH_2CH_2NH\underset{\underset{COONa}{|}}{C}HCH_2SO_3Na$$

| | M/Z |
|---|---|
| $(T-3Na + 2H)^{-2}$ | 311 |
| $(T-4Na + 4H)^{-2}$ | 301 |
| $(T-5Na + 4H)^{-2}$ | 290 |
| $(T-6Na + 5H)^{-2}$ | 279 |
| $(T-6Na + 5H)^{-3}$ | 186 |

The above EMS analysis of crude $Na_4EDC$ suggests a mixture of EDC and $NA_6EDC$ trimer. The latter product can be used in the same manner as EDC and is, therefore, useful as a chelant/sequestrant for detergent, personal product, oral hygiene, cosmetic, food, pharmaceutical and industrial applications.

Preparation of Pure Ethylene Dicysteate (EDC)

24 g (0.128 mol) of cysteic acid was dissolved in 160 ml of water and 10.2 g (0.255 mol) of sodium hydroxide was added. After dissolution, 6.8 g (0.064) sodium carbonate was added, followed by 80 ml ethanol. While refluxing the solution, 14.4 g (0.077 mol) dibromoethane was added gradually during a period of 4 hours, followed by refluxing overnight. An additional 14.4 g (0.077 mol) of dibromoethane was added, followed by all-day reflux. The solution was distilled to remove solvents and the resulting solid which contains EDC, and other materials was recovered and triturated with methanol/water. The purified solid was triturated again with methanol only and stirred overnight to remove residual materials, followed by dissolution in 10 cc water. Adjustment of the solution pH to 5.1–5.3 precipitates out 2.1 g of pure EDC.

Carbon 13 Nuclear Magnetic Resonance ($C^{13}$ NMR) Analysis (ppm, $D_2O$/TSP)

$$NaO_3S\overset{2}{C}H_2\overset{3}{C}HNH\overset{5}{C}H_2\overset{5}{C}H_2NH\overset{3}{C}H\overset{2}{C}H_2SO_3Na$$
$$\underset{COONa}{|}\qquad\underset{COONa}{|}$$

$Na_4EDC$ (Pure)

| | Predicted (H, acid form) | Found (Na, sodium form) |
|---|---|---|
| $C^2$ | 40.19 | 48.9 |
| $C^3$ | 54.14 | 62.8 |
| $C^4$ | 174.68 | 181.1 |
| $C^5$ | 53.42 | 55.8 |

The above $C^{13}$ NMR analysis suggests the formation of pure ethylene dicysteic acid tetrasodium salt.

Electrospray Mass Spectrometry (EMS) Analysis II
M=452, $Na_4$ EDC (pure)

| | M/Z |
|---|---|
| $(M-3Na + 2H)^{-}$ | 385 |
| $(M-4Na + 3H)^{-}$ | 363 |
| $(M-3Na + 2H)^{-2}$ | 192 |
| $(M-4Na + 3H)^{-2}$ | 181 |

The above EMS analysis of purified EDC suggests the formation of pure ethylene dicysteic tetrasodium salt.

EXAMPLES 2–5

The following Examples (2–5) represent the frame formulations of the present invention. These Examples are not intended to be limiting to be present invention, but rather to simply further illustrate the additional aspects of the present technology which may be considered by the formulator when manufacturing a wide variety of detergent compositions comprising EDC chelant/sequestrant. Numerous modifications and variations are possible without departing from the spirit and scope of the present frame formulations. Unless otherwise indicated, all percentages herein are by weight.

EXAMPLE 2

General Frame Formulations for Heavy-Duty Detergent Powder

| INGREDIENTS (BY WEIGHT) | USA CANADA AUSTRALIA | SO. AMERICA MIDDLE EAST AFRICA | EUROPE | JAPAN |
|---|---|---|---|---|
| Cleansing agents | 8–30 | 10–32 | 8–28 | 5–29 |
| EDC Chelant/ Sequestrant | 0.1–50 | 0.1–50 | 0.1–50 | 0.1–50 |
| Bleach | 0–27 | 0–7 | 0–30 | 0–7 |
| Anti-corrosion agents | 0–25 | 03–12 | 1–9 | 4–15 |
| Builders | 5–45 | 5–45 | 2–35 | 0–25 |
| Cobuilders (alkalis) | 0–35 | 0–40 | 0–15 | 5–20 |
| Optical brighteners | 0–0.5 | 0–0.5 | 0–0.4 | 0–0.9 |
| Anti-redeposition agents | 0–3 | 0.2–2 | 0.3–4 | 0–2 |
| Enzymes | 0–2.7 | 0–0.8 | 0–1 | 0–0.8 |
| Foam-boosting agents | 0–2 | 0–2 | 0–2 | — |
| Suds-suppression agents | 0.01–3.5 | 0.01–3 | 0.01–4 | 0.01–3 |
| Fillers | 5–45 | 5–39 | 5–45 | 3–45 |
| Water | 6–20 | 6–13 | 4–20 | 5–10 |
| Additional detersive ingredients | Balance | Balance | Balance | Balance |

EXAMPLE 3

Additional Frame Formulations for Heavy-Duty
Detergent Powders

| INGREDIENTS (BY WEIGHT) | USA | EUROPE | JAPAN |
|---|---|---|---|
| Anionic Surfactants | | | |
| Alkylbenzene sulfonates | 5–20 | 5–22 | 5–27 |
| Alkyl sulfates | 0–20 | 0–25 | 0–15 |
| Alkyl ether sulfates | 0–20 | — | — |
| α-Olefin sulfonates | 0–15 | 0–15 | 0–15 |
| Nonionic Surfactants | | | |
| Alcohol ethoxylates | 3–17 | 3–12 | 0–10 |
| Nonylphenol ethoxylates | 0–5 | 0–5 | — |
| Alkyl polyglycosides | 0–15 | 0–15 | 0–15 |
| Alkyl methyl glycamides | 0–18 | 0–18 | 0–18 |
| Alkyl Aldonamides/Aldobionamides | 0–25 | 0–25 | 0–25 |
| EDC Chelant/Sequestrant | 0.1–50 | 0.1–50 | 0.1–50 |
| Bleaching Agents | | | |
| Sodium perborate | 0–27 | 0–30 | 0–7 |
| Sodium percarbonate | 0–27 | 0–30 | 0–7 |
| Bleach Activators | | | |
| Tetraacetyl ethylenediamine (TAED) | 0–5 | 0–8 | 0–8 |
| Sodium nonanoyloxybenzene sulfonate | 0–10 | 0–10 | 0–7 |
| Manganese IV complex agent | 0–0.5 | 0–0.5 | 0–0.5 |
| Anti-Corrosion Agents | | | |
| Sodium silicate | 0–25 | 1–9 | 4–15 |
| Builders (Ion Exchange) | | | |
| Zeolites | 5–49 | 2–35 | 0–25 |
| Polyacrylates | 0–9 | 0–8 | 0–7 |
| Builders | | | |
| Sodium citrate | 0–18 | 0–5 | 5–23 |
| Sodium tartrate mono-/disuccinate | 0–15 | 0–5 | — |
| Co-builders (Alkalis) | | | |
| Sodium carbonate | 0–35 | 0–15 | 5–20 |
| Co-chelating Agents | | | |
| Ethylene diaminetetraacetates (EDTA) | 0–1 | 0–0.5 | — |
| Optical Brighteners | | | |
| Stilbene-disulfonic acid - derivatives | 0–0.5 | 0–0.4 | 0–0.9 |
| Bis-(styryl)-biphenyl derivatives | 0–0.5 | 0–0.4 | 0–0.9 |
| Anti-Redeposition Agents | | | |
| Sodium carboxymethyl cellulose | 0–1.5 | 0.3–2 | 0–2.8 |
| Cellulose ethers | 0–1.5 | 0.3–2 | 0–2 |
| Polyethylene glycols | 0–3 | 0–4 | 0–2 |
| Enzymes | | | |
| Proteases | 0–2.7 | 0–1 | 0–0.8 |
| Amylases | 0–1 | 0–1 | 0–0.8 |
| Foaming Boosting Agents | | | |
| Alkanolamides | 0–2 | 0–2 | — |
| Suds-Suppression Agents | | | |
| Silicon oils | 0.01–1 | 0.01–4 | 0.01–3 |
| Fatty acid soaps | 0–3.5 | 0–4 | 0–3 |
| Fabric Softening Agents | | | |
| Quats | 0–5 | — | 0–6 |
| Clays | 0–5 | — | 0–6 |
| Fillers | | | |
| Sodium sulfate | 5–45 | 3–45 | 30–45 |
| Fragrances | 0–1 | 0–1 | 0–1 |
| Dyes/Blueing Agents | 0–1 | 0–1 | 0–1 |

| INGREDIENTS (BY WEIGHT) | USA | EUROPE | JAPAN |
|---|---|---|---|
| | -continued | | |
| Water | 6–20 | 4–20 | 5–10 |
| Formulation Aids | 0–1 | 0–1 | 0–1 |
| Additional Detersive Ingredients | Balance | Balance | Balance |

EXAMPLE 4

Frame Formulations for Heavy-Duty Detergent Liquids (Built and Unbuilt)

| | USA | | EUROPE | | JAPAN | |
|---|---|---|---|---|---|---|
| INGREDIENTS (BY WEIGHT) | BUILT | UNBUILT | BUILT | UNBUILT | BUILT | UNBUILT |
| Anionic Surfactants | | | | | | |
| Alkylbenzene sulfonates | 5–27 | 0–20 | 5–17 | 10–25 | 5–25 | 0–23 |
| Alkyl sulfates | 0–15 | 0–15 | 0–22 | 0–25 | 0–23 | 0–18 |
| Alkyl ether sulfates | 0–25 | 0–22 | 0–20 | 0–22 | 5–20 | 15–25 |
| α-Olefin sulfonates | 0–14 | — | — | 0–15 | 0–20 | — |
| Nonionic Surfactants | | | | | | |
| Alcohol ethoxylates | 5–11 | 15–35 | 2–10 | 10–15 | 4–10 | 10–35 |
| Nonylphenol ethoxylates | 0–15 | 0–15 | 0–12 | 0–14 | 0–14 | 0–14 |
| Alkyl polyglycosides | 0–15 | 0–15 | 0–12 | 0–14 | 0–15 | 0–15 |
| Alkyl methyl glycamides | 0.1–45 | 0.1–45 | 01–45 | 0.1–45 | 0.1–45 | 0.1–45 |
| Alkyl Aldonamides/Aldobionamides | 0–45 | 0–45 | 0–45 | 0–45 | 0–45 | 0–45 |
| EDC Chelant/Sequestrant | 0.1–50 | 0.1–50 | 0.1–50 | 0.1–50 | 0.1–50 | 0.1–50 |
| Anti-Corrosion Agents | | | | | | |
| Sodium silicate | 0–12 | — | — | 0–3 | 3–7 | — |
| Builders | | | | | | |
| Sodium citrate | 1–12 | — | 1–5 | — | 3–7 | — |
| Co-cheleting Agents | | | | | | |
| Ethylene diaminetetraacetates (EDTA) | — | — | — | 0–3 | 0–3 | 0–5 |
| Optical Brighteners | | | | | | |
| Stilbene-disulfonic acid-derivatives | 0–0.3 | 0–0.3 | 0–0.3 | 0–0.3 | 0–0.4 | 0–0.4 |
| Bis-(styryl)-biphenyl derivatives | 0–0.4 | 0–0.4 | 0–0.4 | 0–0.4 | 0–0.4 | 0–0.4 |
| Enzymes | | | | | | |
| Proteases | 0–1.8 | 0–2.5 | 0–0.5 | 0–1 | 0–0.5 | 0–1 |
| Enzyme Stabilizing Agents | | | | | | |
| Triethanolamine | 0–3 | 0–4 | 0–3 | 0–4 | 0–5 | 0–5 |
| Foaming Boosting Agents | | | | | | |
| Alkanolamides | — | — | 0–2 | — | — | — |
| Suds-Suppression Agents | | | | | | |
| Fatty acid soaps | — | — | 0–2 | — | — | — |
| Fabric Softening Agents | | | | | | |
| Quats | 0–2 | — | — | — | — | — |
| Clays | 0–2 | — | — | — | — | — |
| Hydrotropes/Solubilizing Agents | | | | | | |
| Xylene sulfonates | 0–14 | 0–12 | 0–6 | 0–12 | 0–15 | 0–15 |
| Ethanol | 7–14 | 5–12 | 3–6 | 6–12 | 10–15 | 5–15 |
| Propylene glycol | 7–14 | 5–12 | 3–10 | 6–14 | 5–15 | 5–18 |
| Fragrances | 0–1 | 0–1 | 0–1 | 0–1 | 0–1 | 0–1 |
| Dyes/Blueing Agents | 0–1 | 0–1 | 0–1 | 0–1 | 0–1 | 0–1 |
| Water and Additional Detersive Ingredients | Balance | Balance | Balance | Balance | Balance | Balance |

EXAMPLE 5

Frame Formulations for Light-Duty Dishwashing Detergent Liquids

| INGREDIENTS (BY WEIGHT) | DISHWASHING LIQUID |
|---|---|
| Anionic Surfactants | |
| Alkylbenzene sulfonates | 1–25 |
| Alkyl sulfates | 2–10 |
| Alkyl ether sulfates | 2–23 |
| Fatty acid soaps | 0–3 |
| Nonionic Surfactants | |
| Alcohol ethoxylates | 0–15 |
| Alkyl polyglycosides | 0–20 |
| Alkyl methyl glycamides | 0–18 |
| Alkyl Aldonamides/Aldobionamides | 0–30 |
| Amphoteric Surfactants | |
| Alkyl betaines | 0–3 |
| EDC Chelant/Sequestrant | 0.1–50 |
| Builders | |
| Sodium citrate | 0–5 |
| Co-chelating Agents | |
| Ethylene diaminetetraacetates (EDTA) | 0–3 |
| Foaming Boosting Agents | |
| Alkanolamides | 0–8 |
| Hydrotropes/Solubilizing Agents | |
| Xylene sulfonates | 0–2 |
| Ethanol | 0–10 |
| Viscosity Modifying Agent | |
| Sodium chloride | 0–4 |
| Ions | |
| Magnesium sulfate | 0–2 |
| Opacifiers | 0–2 |
| Fragrances | 0–1 |
| Dyes | 0–1 |
| Water and Additional Detersive Ingredients | Balance |

EXAMPLES 6–11

To further demonstrate the stain removal characteristics of detergent compositions containing EDC, a commercial detergent composition was obtained containing EDC and compared to an identical composition containing either NTA, EDTA or DETPA. The latter chelates, EDTA and DETPA are not readily biodegradable. The structure of the chelants are as follows:

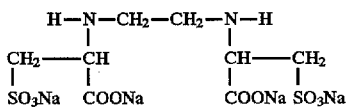

EDC (The Invention)

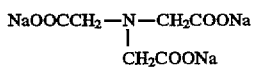

NTA (Comparative)

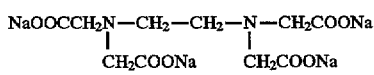

EDTA (Comparative)

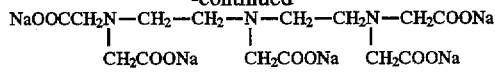

DEPTA (Comparative)

A great number of test methods have been developed to determine the performance of detergents and various detergent ingredients. A preferred, well-accepted test method involves applying various soils uniformly to a standard cloth under strict specifications yielding an "artificially soiled test cloth", which is then washed under controlled conditions in a Terg-o-tometer (washing machine simulator). The detergency of the surfactant is assessed electronically using a reflectometer (Colorgard 2000). Before washing, the initial reflectance value of the soiled test cloth is measured (front and back) giving a value which is represented as reflectance-soiled ($R_s$). After washing, the final reflectance value of the soiled test cloth is measured (front and back) giving a value which is represented as reflectance-washed ($R_w$). From these values, the differences in reflectance $\Delta R = R_w - R_s$ can be calculated and used as a measure of soil removal. It shall be understood that higher $\Delta R$ values suggests better or enhanced detergency.

In general, textiles come in contact with a variety of soils, some of which are complicated mixtures of materials differing in their chemical and physical structure. The selection of a model soil representing a natural "real life" soil is a complicated problem. However, significant progress has been made in the area of fabric washing making artificial soiling more realistic. Since it is not practical to test the surfactant detergency with every possible soil that may be encountered, it must therefore be limited to typical model soils representing the most common natural soils. Artificial soils are usually selected to represent the following four types of common natural soils which includes (1) particulate soils, (2) fatty soils, (3) stains and (4) oily soils.

The stain removal characteristics of EDC was determined on EMPA 114 cloth, CS-15, test fabrics coffee cloth, test fabrics tea cloth and WFK 20D cloth. Each of the cloths were soiled with the following materials:

| CLOTH | SOIL |
|---|---|
| EMPA 114 | Cotton cloth soiled with red wine (stain) |
| CS-15 | Cotton cloth soiled with blueberry (stain) |
| Test fabrics coffee | Cotton cloth soiled with coffee (stain) |
| Test fabrics tea | Cotton cloth soiled with tea (stain) |
| WFK 20D | Polyester/cotton cloth (65:35) soiled with pigment and sebum (particulate, fatty and oily soil) |

The WFK synthetic pigment consists of:

| | |
|---|---|
| 86.0% | Kaolinite |
| 8.0% | Flame Soot 101 |
| 4.0% | Iron Oxide Black |
| 2.0% | Iron Oxide Yellow |
| 100% | |

The WFK synthetic sebum consists of:

| | |
|---|---|
| 18.0% | Free Fatty Acids |
| 32.8% | Beef Tallow |
| 3.6% | Fatty Acid Triglycerides |
| 18.3% | Lanoline |
| 3.7% | Cholesterol |
| 12.0% | Hydrocarbon Mixture |
| 11.6% | Cutina |
| 100% | |

The wash conditions used to evaluate EDC are as follows:

| Wash Conditions for EDC | |
|---|---|
| Apparatus | Terg-o-tometer |
| Wash Time | 20 mins. |
| Agitation | 70 rpm |
| Wash Liquid Volume | 1000 ml |
| Base Liquid | Wisk |
| Dosage | 6.0 g/l |
| pH | 8.5 |
| Hardness | 24 FH (4:1 Ca:Mg) |
| Metal ions | 2.3 ppm $Zn^{+2}$, 2 ppm $Fe^{+3}$, 1.1 ppm $Cu^{+2}$, 0.12 ppm $Mn^{+2}$ |
| Temperature | 40° C. |
| Test cloths | Four 3 × 4 cloths per pot (single stain) |
| Washes | 1 to 3 separate washes |

Order of Procedure:

1) DI water, hardness and metal ions
2) Wisk liquid detergent
3) Sequestrant
4) Cloth
5) Wash (20 min)
6) Rinse (1 min)
7) Dryer (10 min)

Sequestrant:

a) EDC (The Invention)
b) NTA (Comparative)
c) EDTA (Comparative)
d) DETPA (Comparative)

Sequestrant Concentration: 3–7% by weight of Wisk detergent formulation.

A commercially available heavy duty liquid detergent (Wisk) was used with various levels of EDC (3–7%). This was compared to an identical composition containing either NTA, EDTA or DETPA. The test was performed in a terg-o-tometer. Water containing the appropriate hardness and heavy metal ions were added followed by the addition of Wisk liquid detergent. The chelant was then added to the wash water in an amount sufficient to make the levels of the chelant either 3% or 7% by weight of the liquid detergent. Finally, artificially soiled 3×4 fabrics were added and washed for 20 mins. The fabrics were than rinsed and dried in a dryer. One or three replicates of each treatment was conducted. The mean scores for each treatment were calculated and are represented as ΔR. It shall be understood that higher ΔR values suggest better or enhanced detergency/cleaning. A statistical value was assigned to each score at a 95% confidence limit to counterbalance any variation associated with the test and to provide a reliable range associated with the mean. The results are shown below in Examples 6–11.

EXAMPLE 6

Stain Removal Characteristics of Chelants in Wisk Liquid Detergent EMPA 114 (Red Wine)

| CHELANT | Three Wash Mean (ΔR) | | 95% CONFIDENCE LIMIT | |
|---|---|---|---|---|
| | | | Low | High |
| 0% (No Chelant) | 20.5 ± 0.2 | = | 20.3 | 20.7 |
| 7% EDC (The Invention) | 24.4 ± 0.4 | = | 24.0 | 24.8 |
| 7% NTA (Comparative) | 23.5 ± 0.3 | = | 23.2 | 23.8 |
| 7% EDTA (Comparative) | 24.9 ± 0.2 | = | 24.7 | 25.1 |
| 7% DETPA (Comparative) | 24.4 ± 0.2 | = | 24.2 | 24.6 |

From the above table, it can be seen that EDC, with a higher mean ΔR value, provides improved cleaning on polyphenolic red wine stain over the Wisk formulation without a chelant (0%). This improvement was found to be statistically equivalent to EDTA and DETPA, but statistically better than NTA. This finding is new and has not been disclosed in the art.

EXAMPLE 7

Stain Removal Characteristics of EDC in Wisk Liquid Detergent CS-15 (Blueberry)

| CHELANT | One Wash Mean (ΔR) | | 95% CONFIDENCE LIMIT | |
|---|---|---|---|---|
| | | | Low | High |
| 0% (No Chelant) | 30.7 ± 0.6 | = | 30.1 | 31.3 |
| 3% EDC | 33.5 ± 0.8 | = | 32.7 | 34.3 |

From the above table, it can see that EDC, with a higher mean ΔR value, provides improved cleaning on polyphenolic blueberry stain. This improvement was found to be statistically better than the Wisk formulation without a chelant (0%).

EXAMPLE 8

Stain Removal Characteristics of EDC in Wisk Liquid Detergent Test Fabrics Coffee

| CHELANT | One Wash Mean (ΔR) | | 95% CONFIDENCE LIMIT | |
|---|---|---|---|---|
| | | | Low | High |
| 0% (No Chelant) | 25.9 ± 0.6 | = | 25.3 | 26.5 |
| 3% EDC | 29.2 ± 0.6 | = | 28.6 | 29.8 |

From the above table, it can see that EDC, with a higher mean ΔR value, provides improved cleaning on polyphenolic coffee stain. This improvement was found to be statistically better than the Wisk formulation without a chelant (0%).

EXAMPLE 9

Stain Removal Characteristics of EDC in Wisk Liquid Detergent

| CHELANT | One Wash Mean (ΔR) | | 95% CONFIDENCE LIMIT | |
|---|---|---|---|---|
| | | | Low | High |
| 0% (No Chelant) | 15.4 ± 0.5 | = | 14.9 | 15.9 |
| 3% EDC | 21.1 ± 0.7 | = | 20.4 | 21.8 |

From the above table, it can see that EDC, with a higher mean ΔR value, provides improved cleaning on polyphenolic tea stain. This improvement was found to be statistically better than the Wisk formulation without a chelant (0%). This find has not been disclosed in the art.

EXAMPLE 10

Stain Removal Characteristics of EDC in Wisk Liquid Detergent WFK 20D (Pigment/Sebum)

| CHELANT | One Wash Mean (ΔR) | | 95% CONFIDENCE LIMIT | |
|---|---|---|---|---|
| | | | Low | High |
| 0% (No Chelant) | 10.4 ± 0.5 | = | 9.9 | 10.9 |
| 3% EDC | 11.1 ± 0.4 | = | 10.7 | 11.5 |

From the above table, it can see that EDC, with a higher mean ΔR value, provides improved cleaning an oily soil. However, this improvement was found to be statistically the same as the Wisk formulation without a chelant (0%).

EXAMPLE 11

Stain Removal Characteristics of Chelants in Wisk Liquid Detergent CS-14 (Morello Juice)

| CHELANT | One Wash Mean (ΔR) | | 95% CONFIDENCE LIMIT | |
|---|---|---|---|---|
| | | | Low | High |
| 0% (No Chelant) | 6.5 ± 0.3 | = | 6.2 | 6.8 |
| 3% EDC (The Invention) | 12.6 ± 0.7 | = | 11.9 | 13.3 |
| 3% NTA (Comparative) | 10.6 ± 0.4 | = | 10.2 | 11.0 |
| 3% EDTA (Comparative) | 10.5 ± 0.2 | = | 10.3 | 10.7 |
| 3% DETPA (Comparative) | 11.6 ± 0.5 | = | 11.1 | 12.1 |

From the above table, it can be seen that EDC, with a higher mean ΔR value, provides improved cleaning on polyphenolic morello juice (cherry juice) stain over the Wisk formulation without a chelant (0%). This improvement was found to be statistically equivalent to DETPA, but statistically better than NTA and EDTA. This finding is new and has not been disclosed in the art.

EXAMPLE 12

The EDC component of Examples 2–5 is replaced by EDC trimer at the same levels of incorporation.

EXAMPLE 13

The EDC component of Examples 2–5 is replaced by a mixture of EDC trimer and EDC at the same levels of incorporation.

EXAMPLE 14

Preparation of 2-Hydroxypropylene Dicysteate (HPDC)

24 g (0.128 mol) of cysteic acid is dissolved in 160 ml of water and 10.2 g (0.255 mol) of sodium hydroxide is added. After dissolution, 6.8 g (0.064) sodium carbonate is added, followed by 80 ml ethanol. While refluxing the solution, 16.8 g (0.077 mol) 1,3-dibromo-2-propanol is added gradually during a period of 4 hours, followed by refluxing overnight. An additional 16.8 g (0.077 mol) of 1,3-dibromo-2-propanol is added, followed by all-day reflux. The solution is distilled to remove solvents and the resulting solid which contains HPDC and other materials is recovered and triturated with methanol/water. The purified solid is triturated again with methanol only and stirred overnight to remove residual materials, followed by dissolution in 10 cc water. Adjustment of the solution pH to 3–5 precipitates out pure HPDC.

EXAMPLE 15

The EDC component of Examples 2–5 is replaced by HPDC at the same levels of incorporation.

EXAMPLE 16

The EDC component of Examples 2–5 is replaced by a mixture of HPDC and EDC at the same levels of incorporation.

What is claimed is:

1. A compound of the formula:

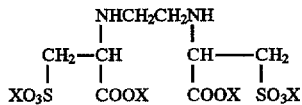

wherein X is independently selected from the qroup consisting of hydrogen, sodium, potassium, lithium, ammonium, monoethanolammonium, diethanolammonium, triethanolammonium or mixtures thereof.

2. A compound as defined in claim 1 wherein X is hydrogen.

3. A compound as defined in claim 1 wherein X is sodium.

4. A compound as defined in claim 1 wherein X is monoethanolamine.

5. A compound as defined in claim 1 wherein X is triethanolamine.

6. A compound of the formula:

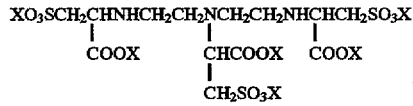

wherein X is independently selected from the group consisting of hydrogen, sodium, potassium, lithium, ammonium, monoethanolammonium, diethanolammonium, triethanolammonium or mixtures thereof.

7. A compound as defined in claim 6 wherein X is hydrogen.

8. A compound as defined in claim 6 wherein X is sodium.

9. A compound as defined in claim 6 wherein X is monoethanolamine.

10. A compound as defined in claim 6 wherein X is triethanolamine.

11. A compound of the formula:

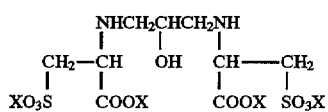

wherein X is independently selected from the group consisting of hydrogen, sodium, potassium, lithium, ammonium, monoethanolammonium, diethanolammonium, triethanolammonium or mixtures thereof.

12. A compound as defined in claim 11 wherein X is hydrogen.

13. A compound as defined in claim 11 wherein X is sodium.

14. A compound as defined in claim 11 wherein X is monoethanolamine.

15. A compound as defined in claim 11 wherein X is triethanolamine.

* * * * *